(12) United States Patent
Hendren et al.

(10) Patent No.: US 11,697,527 B1
(45) Date of Patent: Jul. 11, 2023

(54) TAMPER EVIDENT CLOSURE ASSEMBLY

(71) Applicants: Logan Hendren, Hypoluxo, FL (US); Jonathan Vitello, Ft. Lauderdale, FL (US); Peter Lehel, Boca Raton, FL (US)

(72) Inventors: Logan Hendren, Hypoluxo, FL (US); Jonathan Vitello, Ft. Lauderdale, FL (US); Peter Lehel, Boca Raton, FL (US)

( * ) Notice: Subject to any disclaimer, the term of this patent is extended or adjusted under 35 U.S.C. 154(b) by 0 days.

(21) Appl. No.: 17/018,583

(22) Filed: Sep. 11, 2020

Related U.S. Application Data

(60) Provisional application No. 62/898,669, filed on Sep. 11, 2019.

(51) Int. Cl.
*B65D 41/46* (2006.01)
*B65D 55/06* (2006.01)

(52) U.S. Cl.
CPC .......... *B65D 41/46* (2013.01); *B65D 55/066* (2013.01); *B65D 2251/0015* (2013.01); *B65D 2251/0093* (2013.01); *B65D 2401/15* (2020.05)

(58) Field of Classification Search
CPC .. B65D 41/46; B65D 55/066; B65D 2401/26; B65D 2251/0015
USPC ....................................................... 215/250
See application file for complete search history.

(56) References Cited

U.S. PATENT DOCUMENTS

| | | |
|---|---|---|
| 722,943 A | 3/1903 | Chappell |
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |

(Continued)

FOREIGN PATENT DOCUMENTS

| | | |
|---|---|---|
| DE | 202008018507 | 2/2015 |
| EP | 0148116 | 7/1985 |

(Continued)

OTHER PUBLICATIONS

Arai Tsugio, Pilfering Proof Cap, Jan. 1, 1996.

*Primary Examiner* — J. Gregory Pickett
*Assistant Examiner* — Niki M Eloshway
(74) *Attorney, Agent, or Firm* — Malloy and Malloy, PL; Jennie S. Malloy; Peter A. Matos

(57) ABSTRACT

A closure assembly for a medical container having a sleeve with a tip cap disposed therein in an accessible position relative to an access opening. A cover is fixedly secured to one end of said sleeve, opposite to said access opening and a retainer is fixedly secured within the sleeve, adjacent the cover and in a removably retaining engagement with the tip cap. The removably retaining engagement includes the retainer having one or more segments disposed in retaining engagement with an exterior of the tip cap. Upon detachment of the tip cap from the retainer and the removal thereof from the sleeve, the one or more segments are separable from one another and/or a remainder of the retainer, while being maintained in a captured position within the sleeve.

19 Claims, 3 Drawing Sheets

(56) References Cited

U.S. PATENT DOCUMENTS

| | | |
|---|---|---|
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |
| 3,489,268 A | 1/1970 | Meierhoefer |
| 3,574,306 A | 4/1971 | Alden |
| 3,598,120 A | 8/1971 | Mass |
| 3,610,241 A | 10/1971 | LeMarie |
| 3,674,181 A | 7/1972 | Marks et al. |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,106,621 A | 8/1978 | Sorenson |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A * | 11/1984 | Ishiwatari ............... B65D 51/18 215/251 |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klien et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,735,617 A | 4/1988 | Nelson et al. |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| D323,392 S | 1/1992 | Bryne |
| 5,078,696 A | 1/1992 | Nedbaluk |
| 5,085,332 A * | 2/1992 | Gettig ............... B65D 51/18 215/249 |
| 5,090,564 A | 2/1992 | Chimienti |
| 5,133,454 A | 7/1992 | Hammer |
| 5,135,496 A * | 8/1992 | Vetter ............... A61M 5/34 604/111 |
| 5,163,922 A | 11/1992 | McElveen, Jr. et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,505,705 A | 4/1996 | Galpin et al. |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,617,954 A | 4/1997 | Kato et al. |
| 5,624,402 A * | 4/1997 | Imbert ............... A61M 5/3134 604/111 |
| 5,662,233 A | 9/1997 | Reid |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Lift et al. |
| 5,776,124 A | 7/1998 | Wald |
| 5,785,691 A * | 7/1998 | Vetter ............... A61M 5/34 215/DIG. 3 |
| 5,797,885 A | 8/1998 | Rubin |
| 5,807,343 A | 9/1998 | Tucker et al. |
| 5,829,589 A | 11/1998 | Nguyen et al. |
| D402,766 S | 12/1998 | Smith et al. |
| 5,842,567 A | 12/1998 | Rowe et al. |
| 5,876,381 A | 3/1999 | Pond et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A * | 9/1999 | Nishida ............... B65D 51/241 215/249 |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsais |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |

(56) References Cited

U.S. PATENT DOCUMENTS

| | | |
|---|---|---|
| 6,439,276 B1 | 8/2002 | Wood et al. |
| 6,485,460 B2 | 11/2002 | Eakins et al. |
| 6,488,666 B1 | 12/2002 | Geist |
| 6,491,665 B1 | 12/2002 | Vetter et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanly et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Anderasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| D581,046 S | 11/2008 | Sudo |
| D581,047 S | 11/2008 | Koshidaka |
| D581,049 S | 11/2008 | Sudo |
| 7,482,166 B2 | 1/2009 | Nollert et al. |
| D589,612 S | 3/2009 | Sudo |
| 7,497,330 B2 | 3/2009 | Anthony et al. |
| 7,503,453 B2 * | 3/2009 | Cronin .............. B65D 51/2892 206/221 |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 8,034,041 B2 | 10/2011 | Domkowski et al. |
| 8,079,518 B2 | 12/2011 | Turner et al. |
| 8,091,727 B2 | 1/2012 | Domkowwski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello et al. |
| 9,220,486 B2 | 12/2015 | Schweiss et al. |
| 9,220,577 B2 | 12/2015 | Jessop et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Ingram et al. |
| D777,903 S | 1/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh et al. |
| D831,201 S | 10/2018 | Holtz et al. |
| D834,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 * | 6/2019 | Vitello .............. A61M 39/1055 |
| 10,315,808 B2 * | 6/2019 | Taylor .................. B65D 41/46 |
| 10,376,655 B2 | 8/2019 | Pupke et al. |
| D859,125 S | 9/2019 | Weagle et al. |
| 10,478,262 B2 | 11/2019 | Niese et al. |
| 10,758,684 B1 | 9/2020 | Vitello et al. |
| 10,773,067 B2 | 9/2020 | Davis et al. |
| 10,888,672 B1 | 1/2021 | Vitello |

(56) References Cited

U.S. PATENT DOCUMENTS

| | | |
|---|---|---|
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1* | 3/2021 | Hunt ................ A61M 5/5086 |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 11,413,406 B1 | 8/2022 | Vitello et al. |
| 11,426,328 B1 | 8/2022 | Ollmann et al. |
| 11,471,610 B1 | 10/2022 | Banik et al. |
| 11,523,970 B1 | 12/2022 | Vitello et al. |
| 11,541,180 B1 | 1/2023 | Vitello et al. |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0046962 A1 | 4/2002 | Vallans et al. |
| 2002/0079281 A1 | 6/2002 | Hierzer et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2003/0187403 A1 | 10/2003 | Balestracci |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0173563 A1 | 9/2004 | Kim et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0169611 A1 | 8/2006 | Prindle |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |
| 2009/0084804 A1 | 4/2009 | Caspary et al. |
| 2009/0099552 A1 | 4/2009 | Levy et al. |
| 2009/0149815 A1 | 6/2009 | Kiel et al. |
| 2009/0166311 A1* | 7/2009 | Claessens ............ B65D 41/28 215/203 |
| 2009/0326481 A1 | 12/2009 | Swisher et al. |
| 2010/0050351 A1 | 3/2010 | Colantonio et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0076840 A1 | 3/2014 | Graux et al. |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0013811 A1 | 1/2015 | Carrel et al. |
| 2015/0048045 A1 | 2/2015 | Miceli et al. |
| 2015/0112296 A1 | 4/2015 | Ishiwata et al. |
| 2015/0136632 A1 | 5/2015 | Moir et al. |
| 2015/0182686 A1 | 7/2015 | Okihara |
| 2015/0191633 A1 | 7/2015 | De Boer et al. |
| 2015/0246185 A1 | 9/2015 | Heinz |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0136352 A1 | 5/2016 | Smith et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Viitello et al. |
| 2016/0194121 A1 | 7/2016 | Ogawa et al. |
| 2016/0250420 A1 | 9/2016 | Maritan et al. |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1* | 8/2017 | Glaser .................. B65D 21/02 |
| 2017/0239141 A1 | 8/2017 | Davis et al. |
| 2017/0297781 A1 | 10/2017 | Kawamura |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0064604 A1 | 3/2018 | Drmanovic |
| 2018/0078684 A1 | 3/2018 | Peng et al. |
| 2018/0089593 A1 | 3/2018 | Patel et al. |
| 2018/0098915 A1 | 4/2018 | Rajagopal et al. |
| 2018/0147115 A1 | 5/2018 | Nishioka et al. |
| 2019/0388626 A1 | 12/2019 | Okihara |
| 2022/0008645 A1 | 1/2022 | Ukai et al. |

FOREIGN PATENT DOCUMENTS

| | | |
|---|---|---|
| GB | 486367 | 6/1938 |
| JP | 08002544 | 1/1996 |
| KR | 101159987 | 6/2012 |
| WO | WO2008000279 | 1/2008 |
| WO | WO2017086607 | 5/2015 |

* cited by examiner

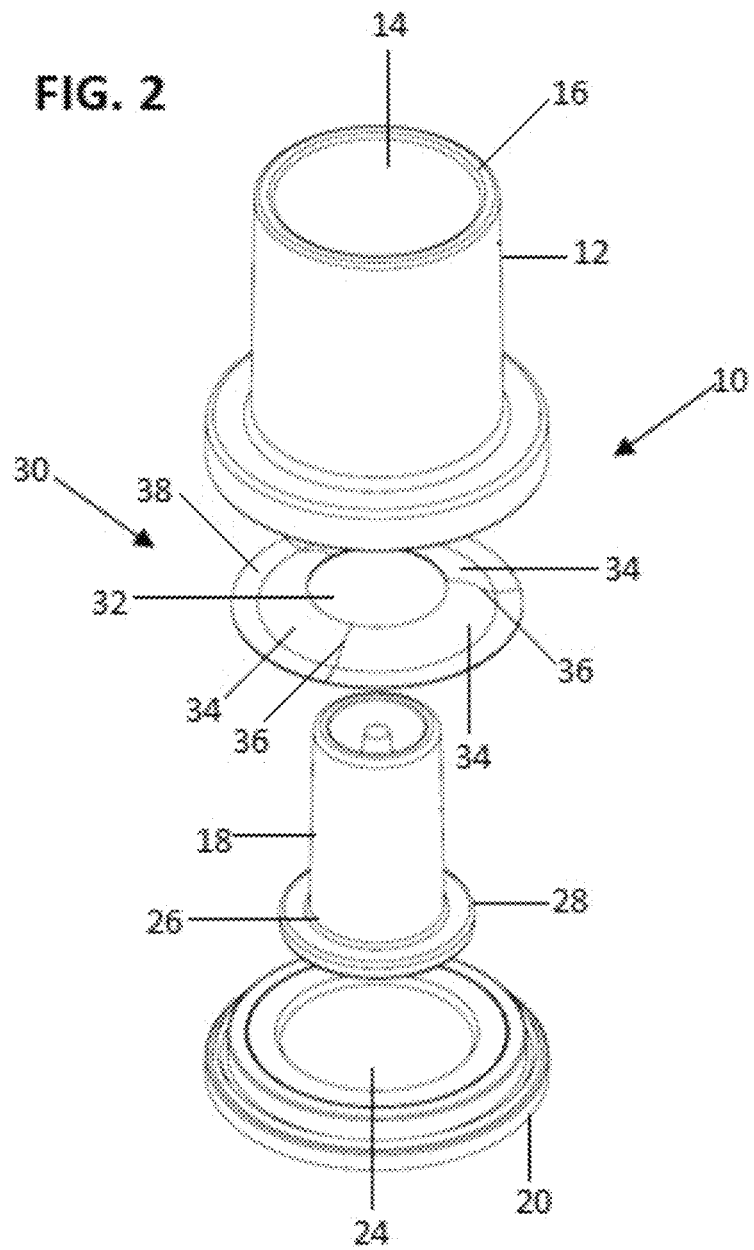

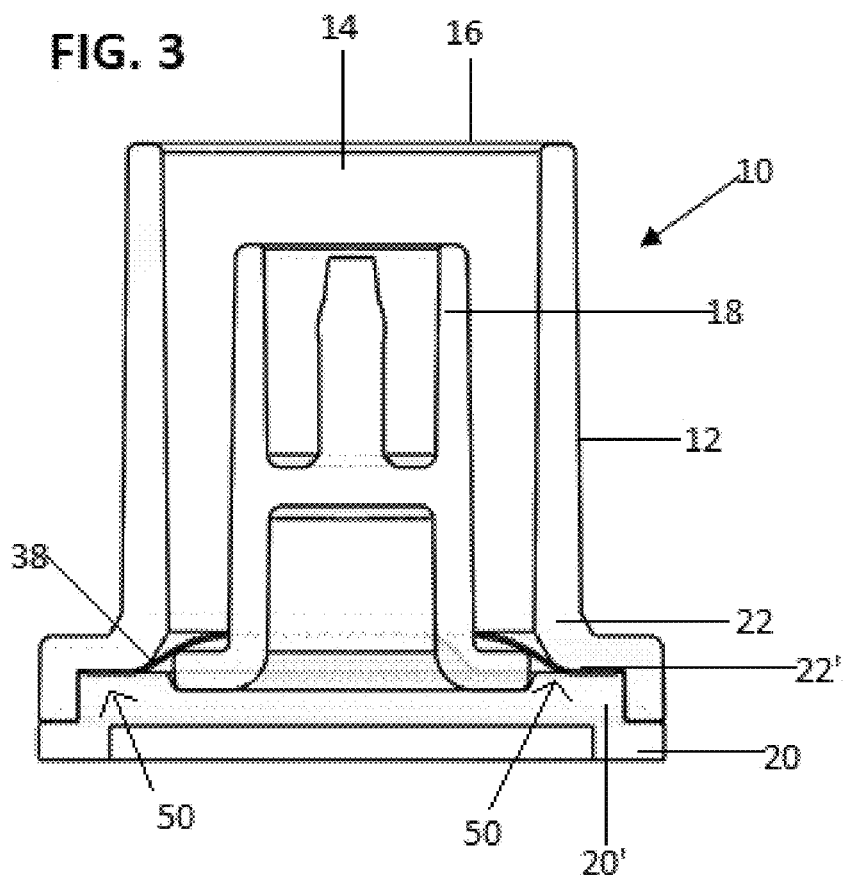

TAMPER EVIDENT CLOSURE ASSEMBLY

This patent application claims priority to a U.S. Provisional patent application, namely, that having Ser. No. 62/898,669 and a filing date of Sep. 11, 2019, with the contents of this prior application being incorporated herein by reference in their entirety.

BACKGROUND OF THE INVENTION

Field of the Invention

This invention is directed to a closure assembly for a medical container having tamper evident capabilities and including a tip cap removably retained within a sleeve by a retainer, preferably formed of separable material. Removal of the tip cap from the sleeve interior results in at least partial separation of portions of the retainer, while being maintained in a captured position within the sleeve.

Description of the Related Art

In the medical field, it is a relatively common for authorized medical personnel to prescribe a drug or medication for a patient which is to be given by injection or other procedures, such as administering fluids to the patient by intravenous (IV) infusion. It is also relatively common procedure for syringes and other drug administering devices to be pre-loaded or filled by pharmacists or other authorized personnel, whether within the hospital or at another facility and location. However, such locations are typically located in a remote part of the hospital or other facility, relative to the patient care area where the injection is to be administered. Indeed, large medical facilities may include a location on the hospital grounds where drugs and other fluids are delivered to multiple nursing stations at different locations. Because of the remote location of many nurse's stations relative to a filling location, a fluid or drug loaded administering device is very often given to another person for delivery to a nurse's station for subsequent dosing of the patient by a duly qualified nurse or other medically trained person. As a result, a pre-loaded syringe may travel quite some distance and be handled by several people before it reaches a nurse's station, which raises some concern that the contents of the syringe may be tampered with or cause the sterility of the syringe and/or its contents to be comprises.

Additionally, in the case where a drug has been prescribed that is a very expensive or addictive, such as but not limited to morphine, has been pre-loaded in the syringe or other administering device, there is a danger that the pre-loaded syringe or other administering device will be tampered with at some point, by a person seeking unauthorized access to the drug. This possibility can present a real danger if such a person were to gain access to the prescribed medicine and then, inappropriately and without concern, substitute some other, unauthorized material in the syringe which looks like the actual prescribed medicine and dosage. By way of an example only, if saline solution or water or another drug were substituted for a dose of morphine, the patient would not receive the prescribed drug which by itself, could be quite harmful, while the substituted content might potentially also cause serious harm. Thus, there is a problem of knowing if a sealed, pre-loaded syringe or other administering device has, or has not, been exposed to contamination or might otherwise have been compromised by its being tampered with.

More specifically, and in order to overcome the disadvantages and concerns associated with the growing use of syringes and/or other medical containers or devices that are pre-filled with various prescribed medicines, a variety of "tamper evident structures" have been developed. Such tamper evident assemblies are structured to prevent or at least restrict access to the contents of a pre-filled syringe. If in fact, access has been accomplished or even attempted to a pre-filled syringe or other drug administering device, such tamper evident assemblies are intended to provide a clear indication of having been tampered with.

In the field relating to closures for medical devices, it is well known that packaging, dispensing, installation, etc. of such tamper evident closures are preferably done in a relatively sterile environment. Therefore, during such processing of medical closures, it is important to maintain a degree of sterility. This is due at least in part to the fact that such tamper evident closures may be attached in closing/sealing relation to a prefilled syringe or other type medical container having medicine or other fluids retained therein. Because the retained medicines and/or fluids are typically intended to be administered to a patient, sterility of the closure may be an important factor.

Moreover, conventional and prior art closures for a variety of different medical containers including, but not limited to preloaded syringes, IV sets, infusion pump cartridge preparations of the type used in various oral, enteral and other pharmacy drug applications, are structured to demonstrate tamper evident capabilities. Frequently, structures associated with such known closures incorporate a ring or other indicator member removably attached within the interior of a housing by one or more breakable, frangible tabs are like structures.

Accordingly, use or attempted access to a contained tip cap during dispensing tip involves removal of the exterior housing, which in turn results in a breakage or separation of the indicator ring or like structure from the housing, along with the tip cap. Access to the contained medication or fluid within the syringe or other medical container that involves a removal of the tip cap and frequently removal of the indicator ring or like indicator structure. However, once the indicator ring is broken or separated from the interior of the housing, small parts of the frangible tabs or like breakable connecting structure are exposed to the user, and possibly a patient, during administration and/or removal of the indicator ring from the syringe or other medical container.

Additional disadvantages associated with such known frangible indicators is the design structuring and manufacture of the indicator member and connecting frangible structure in a manner which will survive shipping, handling and inadvertent breakage during attempted access.

Therefore, there is a need in this field of art for a closure assembly which overcomes the problems and disadvantages, of the type set forth above, which still remain in various existing medical closure structures. If any such improved closure assembly were developed, it would preferably include a retainer disposed in removably and retaining engagement with a tip cap and with certain desirable features which allow access to and removal of the tip cap from an exterior housing, while preventing any full breakage or complete disconnection of components of the retainer.

SUMMARY OF THE INVENTION

The present invention is directed to a closure assembly for a medical container such as, but not limited to, a syringe that has been preloaded with a prescribed medicine or other substance, such as a controlled substance, or an IV set, infusion pump or cartridge prepared according to various oral, enteral and other pharmacy drug applications. In addition, the structural and operative features of the inventive closure assembly, in one or more embodiments, include tamper evident capabilities, wherein use and/or access to contents of an associated syringe or other medical container is clearly discernible.

The medical closure assembly of the present invention comprises an external housing or sleeve, including an at least partially hollow interior and an access opening communicating with the interior of the sleeve. The dimension and configuration of the sleeve interior is sufficient to receive a tip cap therein. As such, the tip cap may include a variety of different structural and operative features and may be defined as a Luer, oral, enteral, neuraxial, etc. tip cap.

In addition, in the illustrated embodiments, a cover is fixedly secured to one end of the sleeve, which is preferably oppositely disposed to the aforementioned access opening. Fixed or permanent attachment of the cover to the opposite one end may be accomplished by ultrasonic welding or other types of appropriate fixed attachment serving to maintain a substantially permanent closure of the opposite one end of the sleeve. Moreover, the fixed attachment of the cover to the one end of the sleeve should be such as to accommodate and/or facilitate a fixed attachment of a retainer within the sleeve in removably retaining engagement with the tip cap, as explained in greater detail hereinafter.

Accordingly, the retainer is preferably fixedly secured within the sleeve by cooperative structuring and disposition of a portion thereof with the opposite one end of the sleeve, as well as the cover. Moreover, the fixed attachment of the retainer, as well as the structural and operative features associated therewith, serve to establish a captured position or orientation of the retainer within the sleeve interior, both before and after its removably retaining engagement with the tip cap. Further, the retainer is disposed, structured and configured to overcome problems and disadvantages associated with the known or commercially available medical closures in the prior art.

In more specific terms, and as set forth above, structural features associated with known tamper evident medical closures typically incorporate and indicator member removably attached within the interior of a housing by one or more breakable, frangible tabs or like structures commonly formed of a rigid material. Removal of such indicator members from a housing or sleeve, when use or access to an associated tip cap is attempted, frequently results in particles of the frangible tabs or like structures loosely breaking off or remaining on the indicator member in an exposed position to a user of the medical container/closure.

In order to overcome such problems, at least one embodiment of the retainer of the closure assembly of the present invention is formed of a "separable" material. As used herein the term "separable" and/or "separable material" in describing the structural features and capabilities of the retainer is meant to include a material wherein the different parts thereof are capable of being torn, ripped and/or otherwise separated from one another. As also set forth hereinafter, such separation of portions of the retainer will occur upon removal of the tip cap from the sleeve, but such separable portions will in the preferred embodiments not become completely detached or break off from one another or the remainder of the retainer. Therefore, the retainer of the medical closure assembly of the present invention may have different cooperatively disposed and structured portions or "segments" thereof being separated from one another by being torn, ripped, etc. but not being detached from one another or the retainer. This is clearly a distinguishable advantage as compared to the frangible or breakable tabs used with at least some known or prior art indicator structures and tamper evident medical closures.

Accordingly, at least one embodiment of the retainer of the medical closure assembly of the present invention is formed from a separable foil material. In turn, the foil material may be a metallic, plastic or other appropriate material foil having the "separable" capabilities, as explained in greater detail herein. Further, the "separable" capabilities of the retainer are due, at least in part to it being formed of at least one but preferably a plurality of segments. In at least one preferred embodiment, the one or more separable segments are contiguously connected to one another and/or a remainder of the retainer by a weakened connection and/or connection line as explained hereinafter. Such a weakened connection may be more specifically defined by a perforated connection or attachment, which may interconnect contiguous ones of the one or more segments to one another and/or to a remainder of the retainer.

Additional features of at least one embodiment of the retainer include it having a substantially disk-like configuration and an opening formed therein. As structured, the opening of the retainer may be substantially centrally located, but may also be disposed and/or formed within the retainer in locations other than a central or coaxial location. Further, the opening is dimensioned and configured to receive at least a portion of the tip cap there through such that the inserted portion is disposed on the interior of the retainer. In such an operable and structural configuration, the one or more segments integrated in the retainer are collectively disposed in at least partially surrounding relation to the inserted portion of the tip cap and in overlying removably retaining engagement with exterior portions thereof as further explained hereinafter.

When in its operable position within the interior of the sleeve, the retainer is disposed in removable engagement with exterior portions of the tip cap. Such removably retaining engagement may be defined by the retainer, including the one or more segments integrated therein, being disposed in overlapping, at least partially overlying and retaining relation to exterior portions of the tip cap. In order to facilitate the aforementioned removably retaining engagement of the retainer with exterior portions of the tip cap, a retained structure is formed on the exterior of the tip cap. In at least one embodiment, the retained structure is in the form of an outwardly extending flange integrally or otherwise connected in outwardly extending relation to the exterior of the tip cap and on a portion thereof in communicating and possibly supporting relation with the cover, as well as the opposite, one end to which the cover is fixedly secured. The outwardly extending flange may be disposed in at least partially or completely surrounding relation to the exterior surface of the tip cap adjacent to the opposite one end of the sleeve and cover. The retainer is cooperatively disposed, configured and structured with the tip cap so as to be disposed in overlapping relation thereto. Such an overlapping relation or position of the retainer, including the one or more segments integrated therein defines the aforementioned removably engaging relation of the retainer relative to the tip cap. Therefore, the structural and operative features of the retainer, including the one or more segments and separable material from which they are formed, are such as to at least initially but removably retain the tip cap within the interior of the sleeve in an accessible position relative to the access opening.

Accordingly, a discharge port of a syringe or like structure of a medical container may pass into and through the access opening into attached engagement with the tip cap. Upon removal of the tip cap and attached discharge port of the medical container the one or more segments of the retainer will be separable from one another and/or a remainder of the retainer along the aforementioned weakened or perforated connections. This in turn will allow a disengagement of the tip cap from its retaining engagement with the retainer and its removal from the sleeve interior, through the access opening.

As also set forth above, the retainer will preferably be maintained in a "captured" position on the interior of the sleeve subsequent to its detachment from the tip cap, as the tip cap is removed from the sleeve interior. In at least one embodiment, such a captured position of the retainer is accomplished by an outer periphery thereof being connected adjacent and/or contiguous to the cover and the opposite one end of the sleeve to which the cover is fixedly secured. More specifically, in at least one embodiment the outer peripheral edge or portion of the retainer, including the one or more segments integrated therein, may be disposed in a fixed, clamped and/or "sandwiched" position between the correspondingly disposed interior surface portions of the opposite, closed-end and the correspondingly disposed inner surface portions of the cover. As indicated, the cover is fixedly secured to the opposite one end of the sleeve in covering relation to that portion of the sleeve interior and will be further disposed to clamp the peripheral portions of the retainer and one or more segments thereof between it and correspondingly disposed portions of the opposite, open end.

Therefore, the production procedure associated with the manufacture of at least in one embodiment of the closure assembly of the present invention includes the outer periphery of the retainer and the one or more segments integrated therein being clamped between the corresponding outer periphery of the opposite one end and the cover. A permanent clamping engagement will thereby be maintained with the outer periphery of the retainer resulting in the aforementioned captured position within the sleeve interior. Further, it is of note that one or more embodiments of the retainer is formed of the aforementioned separable material. As a result, the one or more segments and/or a remainder of the retainer will separate from one another upon a removal of the tip cap but will not become detached or break-off from one another, as in known or prior art tamper evident medical closures.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 2 is a perspective view in exploded form of the embodiment of FIG. 1.

FIG. 3 is a longitudinal sectional view of the embodiment of FIGS. 1 and 2.

Like reference numerals refer to like parts throughout the several views of the drawings.

DETAILED DESCRIPTION OF THE PREFERRED EMBODIMENT

Figure 1:
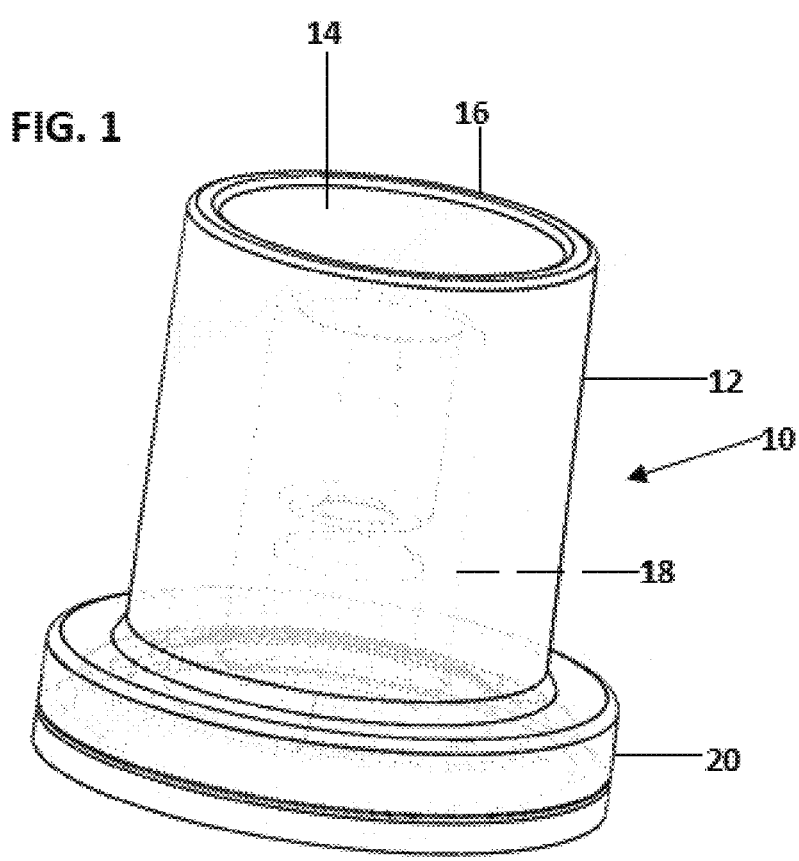
FIG. 1 is a perspective view of the closure assembly of the present invention in an assembled form including a tip cap represented in phantom.

As represented in the accompanying Figures, the present invention is directed to a closure assembly generally indicated as 10 structured to be attached in flow restricting relation to a medical container such as, but not limited to, a preloaded syringe, IV set, etc. In addition, the medical closure assembly 10 is structured to include tamper evident capabilities, which provide a clear indication that tampering with or access to the medical closure assembly 10 and/or the medical container to which it is operatively attached has been attempted.

As such, the closure assembly 10 includes an exterior housing or sleeve 12 having an at least partially hollow interior 14 and an access opening 16 communicating with the interior 14 of the sleeve 12. The sleeve interior 12 is dimensioned and configured to at least initially contain a tip cap 18 therein, as represented in phantom lines in FIG. 1 and in cross-section in FIG. 3. Moreover, the versatility of the closure assembly 10 is demonstrated by the sleeve interior 14 dimensioned and configured to include any one of a possible variety of different tip caps, wherein the structural and operative features thereof may be in the form of a Luer, oral, enteral, neuraxial or other type tip cap. Similarly, the access opening 16 is dimensioned and configured to facilitate removal of the tip cap 18 therethrough, such as when attached to the discharge port of a preloaded syringe or other medical container (not shown for purposes of clarity).

As clearly represented in FIGS. 2 and 3, the medical closure assembly 10 further includes a cover 20 fixedly attached in overlying, closing relation to one end 22, opposite to the access opening 16. The fixed attachment or securement of the cover 20 to the one end 22 may be accomplished by ultrasonic welding or other type connections or attachment, which serve to fixedly and/or permanently maintain the cover 20 attached to the opposite one end 22.

As perhaps best represented in FIGS. 2 and 3, one embodiment of the cover 20 may include a recess or at least partially indented portion 24 cooperatively dimensioned and configured with a corresponding end of the tip cap 18 as at 26. As such, when in the assembled form represented in FIG. 3, the one end 26, including an integrally or fixedly connected retained structure 28, is disposed in at least partially supported relation within the recess 24. However, the cover 20 may include a structural configuration absent the recess 24 and still facilitate the preferred operative disposition of the tip cap 18 relative to a retainer 30 and cover 20.

In the illustrated embodiment, the retainer 30 is fixedly disposed in a captured position within the interior 14 of the sleeve 12 and in removably retaining engagement with the tip cap 18. Such a removably retaining engagement may be at least partially defined by the retainer 30 being disposed in overlapping, retaining engagement with exterior portions of the tip cap 18 and more specifically with the retained structure 28. As further shown in the illustrated embodiment, the retained structure 28 is in the form of an outwardly extending flange integrally or otherwise fixedly connected and extending outwardly from the exterior of the tip cap 18 in at least partially surrounding relation thereto. Such a disposition, configuration and overall structuring of the retained structure 28, facilitates it being retained by the retainer 30. As also more specifically described hereinafter, the removably retaining engagement of the retainer 30 with the tip cap 18 may be at least partially defined by portions and or "segments" 34 thereof being disposed in overlapping retaining engagement with the retained structure 28, as perhaps best represented in FIG. 3.

With primary reference to FIG. 2, additional structural features of the retainer 30 include its being formed in a substantially disk-like configuration having an opening, such as a central opening 32 surrounded by a remaining portion of the retainer 30. It is of note that in the embodiment of FIG. 2, the opening 32 may be centrally or coaxially located relative to the remainder of the retainer 30. However, it should be apparent that the removable retaining engagement of the retainer 30 with the tip cap 18 may be accomplished by the opening 32 being disposed in a location in the retainer 30 other than the aforementioned central location.

Additional features of the retainer 30 include at least one, but preferably a plurality of segments 34, which may vary in number. As represented in the embodiment of FIGS. 2 and 3, the retainer 30 may include a plurality of three segments 34, collectively disposed in contiguous relation to one another. Moreover, each of the one or more segments 34 are initially attached but connected in separable relation to one another by weakened connections 36. Further, in at least one embodiment each of the weekend connections 36 may be in the form of perforated connecting lines, attachments or connections as represented. As also represented, the plurality of segments 34 are collectively disposed in at least partially surrounding relation to the tip cap 18 as it is initially disposed on the interior of the retainer 30, by extending through the opening 32.

In order to overcome known and long recognized problems in the prior art, at least one embodiment of the retainer 30 of the closure assembly 10 is formed of a "separable" material. As used herein, the term "separable" and/or "separable material" in describing the structural features and capabilities of the retainer 30, including segments 34, is meant to describe a material capable of being torn, ripped and/or otherwise separated from one another. Such separation of segments 34 or other portions of the retainer 30 will occur upon removal of the tip cap 18 from the interior 14 sleeve 12. Further, when the segments 34 or other portions of the retainer 30 are separated from one another, they will ideally not become completely detached or break off from one another or the remainder of the retainer 30. Therefore, the retainer 30 of the medical closure assembly 10 may have different cooperatively disposed and structured portions or segments 34 being separated from one another by being torn, ripped, etc., but in the preferred embodiments, not by being detached fully from one another or the retainer 30. This is a clearly distinguishable advantage as compared to the frangible or breakable tabs used with at least some known or prior art indicator structures and tamper evident medical closures.

In addition, at least one embodiment of the retainer 30 of the medical closure assembly 10 is formed from a separable foil material. In turn, the foil material may be a metallic, plastic or other appropriate material and/or foil having the desired "separable" capabilities, as explained in greater detail herein. Further, the "separable" capabilities of the retainer 30 are due, at least in part to it being formed of at least one but preferably a plurality of the segments 34. Such separable capabilities are further enhanced and or facilitated by, the one or more separable segments 34 being formed of the aforementioned separable material and being contiguously connected to one another and/or a remainder of the retainer 30 by the weakened and/or perforated connections 36. Therefore, prior to separation of the segments 34 from one another and/or the remainder of the retainer 30, the retainer 30 will have sufficient structural integrity or strength to retain the tip cap 18 within the interior 14 of the sleeve 16, due to the overlapping, removably engaging relation of the inner ends of the plurality of segments 34 with the retained structure 28. It is worth noting here that if the foil or other material is torn prior to use, the tip cap will not remain inside the sleeve, thereby providing an indicating that the syringe has been tampered with. In addition, in some embodiments, such as where a perforated foil is used, it can be coated with an antiseptic fluid to inhibit or minimize the growth of any bacteria or other microorganisms on the tip cap.

As also shown in the illustrated embodiment of FIG. 3, the retainer 30 will be maintained in a "captured" position on the interior 14 of the sleeve 12 before and subsequent to its detachment from the tip cap 18, as the tip cap 18 is removed from the interior 14 of the sleeve through the access opening 16. Therefore, in at least one embodiment, such a captured position of the retainer 30 as represented in at least FIG. 3, is accomplished by an outer periphery 38 thereof being connected to the cover 20 and the opposite one end 22 to which the cover 20 is fixedly secured. More specifically, in the represented embodiments, the outer peripheral edge or portion 38 of the retainer 30, including the outer peripheral portions, also designated 38, of the one or more segments 34, may be disposed in a fixed, clamped and/or "sandwiched" position, as at 50 in FIG. 3, between correspondingly disposed peripheral or contiguous/adjacent interior surface portions 22' of the opposite, closed-end 22 and the correspondingly disposed, and preferably interior surface portion 20' of the closure 20. As described, the cover 20 is fixedly secured to the opposite one end of 22 the sleeve 12 in covering relation to the portion of the sleeve interior 14, opposite to the access opening 16. In addition, the "captured" position or orientation of the retainer 30 is further meant to describe the one or more segments 34 and/or other portions of the retainer 30 remaining within the interior 14 of the sleeve 12, even when the segments 34 and/or other portions of the retainer are in the "separable" orientation, by being separated from one another but not attached or broken-off from one another.

Therefore, procedures associated with the manufacture of the closure assembly 10 in at least one embodiment, include the outer periphery 38 of the retainer 30, and that of the one or more segments 34, being fixedly clamped and/or sandwiched, as shown in FIG. 3 at 50, between the correspondingly disposed, preferably interior surface portions 22' and 20' respectively, of the opposite one end 22 and the cover 20. The permanent clamping engagement 50 will thereby be maintained with the outer periphery of the retainer 30, resulting in the aforementioned captured position thereof within the interior 14 of the sleeve 12. Further, it is of note that one or more embodiments of the retainer 30 and the one or more segments 34 are formed of the aforementioned separable material. As a result, the one or more segments 34 and/or a remainder of the retainer 30 will separate from one another upon a removal of the tip cap 18, but will in preferred embodiments, not become detached or break-off from one another, as in known or prior art tamper evident medical closures.

Accordingly, a discharge port or like structure of a medical container (not shown) may pass into and through the access opening 16 into attached engagement with the tip cap 18. Upon removal of the tip cap 18 and attached discharge port of the medical container, the one or more segments 34 of the retainer 30 will be separable from one another and/or a remainder of the retainer 30 along the aforementioned weakened or perforated connections 36. This in turn will allow a disengagement of the tip cap 18 from its retained engagement with the retainer 30 and its removal from the interior 14 of the sleeve 12, through the access opening 16.

Since many modifications, variations and changes in detail can be made to the described preferred embodiment of the invention, it is intended that all matters in the foregoing description and shown in the accompanying drawings be interpreted as illustrative and not in a limiting sense. For example, the tamper evident closure assembly described herein may be comprise only four separate pieces such as a sleeve, perforated foil or other material, a tip cap and a bottom cap, and to allow a syringe inserted into the tip cap and pulled out of the sleeve with the perforated foil or other material designed to rip in a controlled manner, with it not possible to reinstall the tip cap into the assembly. However, the scope of the invention should be determined by the appended claims and their legal equivalents.

What is claimed is:

1. A closure for a medical container, said closure comprising:
    a sleeve including an access opening disposed in communicating relation with an interior of said sleeve,
    a tip cap structured for attachment to a discharge port of a medical connector and disposed within said sleeve in an accessible position relative to said access opening,
    a retained structure connected to said tip cap and movable therewith within said sleeve,
    said access opening dimensioned to receive said tip cap therethrough when attached to the medical container, upon removal of said tip cap from said interior of said sleeve,
    a cover fixedly secured to one end of said sleeve opposite to said access opening, in closed, covering relation to said interior of said sleeve,
    a retainer fixedly connected to said sleeve on said interior thereof, initially in an intact, removably retaining engagement with said retained structure of said tip cap,
    said retainer disposed in a captured position within said sleeve, subsequent to detachment of said tip cap and said retained structure there from and removal of said tip cap from the interior of said sleeve, through said access opening, and
    said retainer including at least one segment at least partially separable from a remainder of said retainer by a weakened connection there between.

2. The closure as recited in claim 1 wherein said retainer is at least partially formed of a foil material, capable of being torn.

3. The closure as recited in claim 1 wherein said weakened connection comprises a perforated, separable attachment.

4. The closure as recited in claim 1 wherein said retainer comprises a plurality of contiguously disposed segments removably connected to one another by a plurality of weakened connections.

5. The closure as recited in claim 4 wherein said plurality of segments are fixedly secured, in said captured position, within said sleeve, in separable relation to one another, upon removal of said tip cap from said sleeve.

6. The closure as recited in claim 4 wherein said removably retaining engagement comprises said plurality of segments collectively disposed in at least partially surrounding, engaging relation with said retained structure on an exterior of said tip cap.

7. The closure as recited in claim 1 wherein said fixed connection of said retainer to said sleeve comprises said retainer disposed in fixed, sandwiched engagement concurrently with and between said one end of said sleeve and said cover.

8. The closure as recited in claim 7 wherein said fixed connection of said retainer comprises an outer periphery disposed in said fixed, sandwiched engagement concurrently with and between said one end of said sleeve and said cover.

9. The closure as recited in claim 7 wherein said retainer comprises a plurality of contiguously disposed segments connected in separable relation to one another, said captured position comprising each of said plurality of segments including an outer periphery disposed in said fixed, sandwiched, engagement concurrently with and between said one end of said sleeve and an outer periphery of said cover.

10. The closure as recited in claim 9 wherein said plurality of segments are collectively disposed in at least partially surrounding, removably retaining engagement with said retained structure.

11. The closure as recited in claim 1 wherein said removable, retained engagement comprises said retainer disposed in overlapping, retaining engagement with said retained structure.

12. The closure as recited in claim 11 wherein said retainer comprises an outer periphery disposed in fixed, sandwiched, clamped engagement concurrently with and between said one end of said sleeve and said cover.

13. The closure as recited in claim 11 wherein said removable, retained engagement comprises said tip cap disposed within and extending at least partially through an interior of said retainer, concurrent to said retainer disposed in said overlapping, retaining engagement with said retained structure.

14. The closure as recited in claim 1 wherein said retained structure comprises a flange extending outwardly from and in at least partially surrounding relation to an exterior surface of said tip cap.

15. The closure as recited in claim 14 wherein said retainer comprises a central opening, said tip cap disposed within and extending at least partially through said central opening, concurrent to said retainer disposed in overlapping, retaining engagement with said flange.

16. The closure as recited in claim 15 wherein said retainer comprises a plurality of segments removably connected to one another by a plurality of weakened, perforated connections.

17. The closure as recited in claim 16 wherein said plurality of segments are collectively and initially disposed in overlapping, retaining engagement with said flange, concurrent to an outer periphery of said retainer disposed in fixed, sandwiched engagement with and between said one end of said sleeve and an outer periphery of said cover.

18. A closure for a medical container, said closure comprising:
    a sleeve including an access opening disposed in communicating relation with an interior of said sleeve,
    a tip cap structured for attachment to a discharge port of a medical connector of said sleeve; said tip cap disposed within said sleeve in an accessible position relative to said access opening, said access opening dimensioned to receive said tip cap therethrough when attached to the medical container, upon removal of said tip cap from said interior of said sleeve, a retained structure comprising a flange connected to and extending outwardly from an exterior surface of said tip cap and movable therewith within said sleeve, upon said removal of said tip cap from the interior of said sleeve, a cover fixedly secured to one end of said sleeve opposite to said access opening; said cover disposed in closed, covering relation to said one end and in covering relation to said interior of said sleeve, a retainer fixedly connected to said sleeve and disposed within said sleeve initially in an intact, removably retaining engagement with said retained structure, said retainer comprising a plurality of segments collectively connected in separable, contiguous engagement with one another, said retainer disposed in a fixed, captured position within said sleeve, subsequent to detachment of said tip cap there from and removal of said tip cap from the interior of said sleeve through said access opening, and said intact, removably retaining engagement comprising said retainer disposed in retaining engagement with said retained structure.

19. The closure as recited in claim 18 further comprising said plurality of segments collectively and initially disposed in overlapping, retaining engagement with said flange, concurrent to an outer periphery of said retainer disposed in a fixed, sandwiched, clamped engagement concurrently with and between said one end of said sleeve and an outer periphery of said cover.

* * * * *